United States Patent [19]
Manley

[11] 3,977,392
[45] Aug. 31, 1976

[54] MEDICAL ELECTRODE

[75] Inventor: Arthur G. Manley, Andover, Mass.

[73] Assignee: Eastprint, Inc., Andover, Mass.

[22] Filed: Apr. 21, 1975

[21] Appl. No.: 570,097

[52] U.S. Cl. .............................. 128/2.1 E; 128/417; 128/DIG. 4
[51] Int. Cl.² .......................................... A61B 5/04
[58] Field of Search ............ 128/2.06 E, 2.1 E, 404, 128/410, 411, 416–418, DIG. 4

[56] References Cited
UNITED STATES PATENTS

| | | |
|---|---|---|
| 2,943,627 | 7/1960 | Howell .............................. 128/416 |
| 3,746,004 | 7/1973 | Jankelson ........................ 128/417 |
| 3,774,592 | 11/1973 | Lahr ................................ 128/2.1 E |
| 3,805,769 | 4/1974 | Sessions ........................ 128/2.06 E |
| 3,828,766 | 8/1974 | Krasnow ........................ 128/2.1 E |
| 3,830,229 | 8/1974 | Johnson ........................ 128/2.06 E |
| 3,834,373 | 9/1974 | Sato .............................. 128/2.06 E |
| 3,901,218 | 8/1975 | Buchalter ...................... 128/2.06 E |

FOREIGN PATENTS OR APPLICATIONS

| | | | |
|---|---|---|---|
| 675,494 | 12/1963 | Canada .......................... 128/417 |
| 274,612 | 7/1951 | Switzerland .................... 128/DIG. 4 |

Primary Examiner—Robert W. Michell
Assistant Examiner—Lee S. Cohen
Attorney, Agent, or Firm—Cesari and McKenna

[57] ABSTRACT

A disposable medical electrode has a compliant support layer with an adhesive undersurface. The layer supports a gel pad having a portion exposed at the undersurface and a contact element having a portion exposed at its upper surface. The contact element and gel pad are offset on the support layer with a conductive flexible foil strip extending between them so that movement of the contact element does not disturb the conductive path between that element and the skin area to which the electrode is adhered.

11 Claims, 3 Drawing Figures

U.S. Patent    Aug. 31, 1976    3,977,392
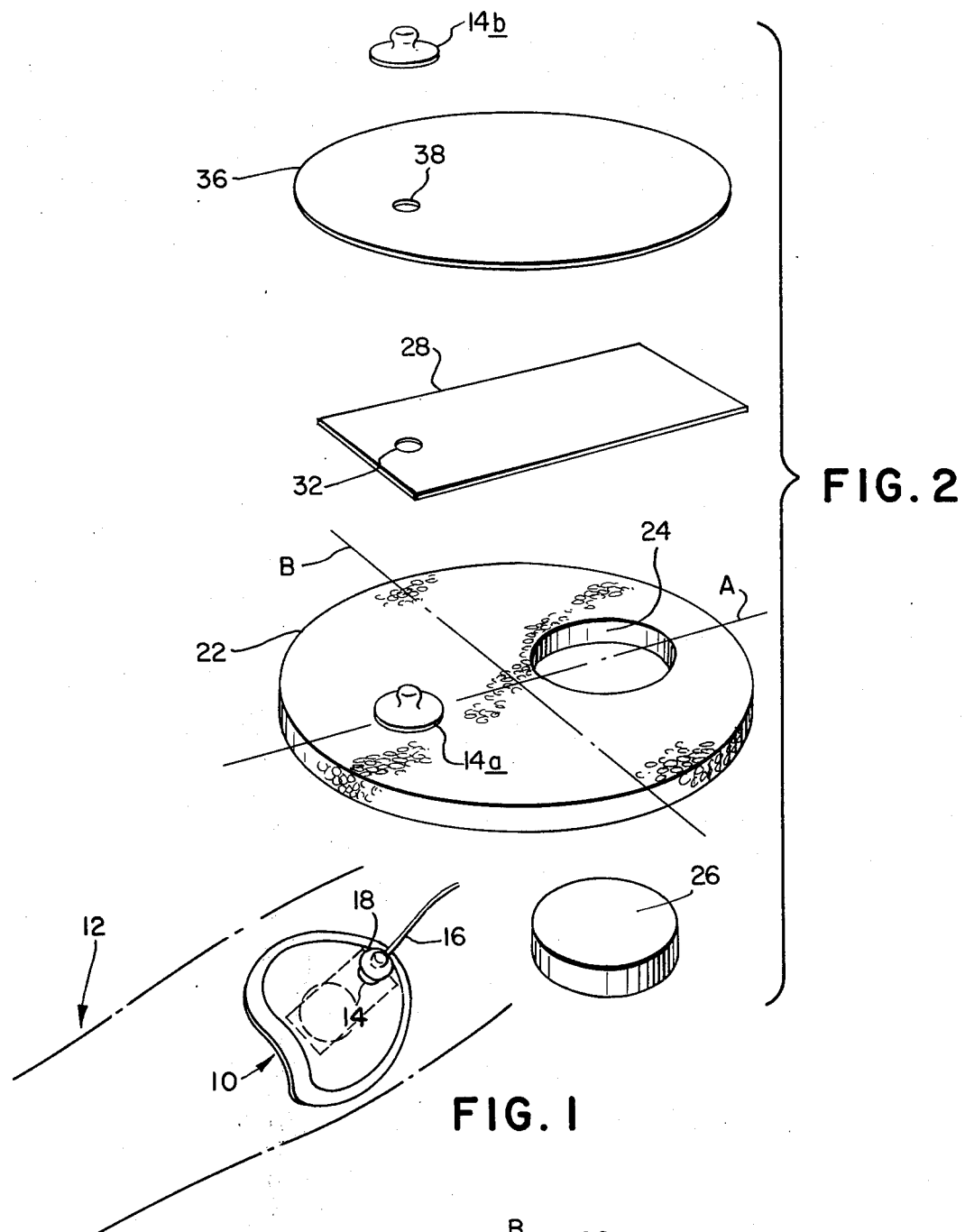
FIG. 2
FIG. 1
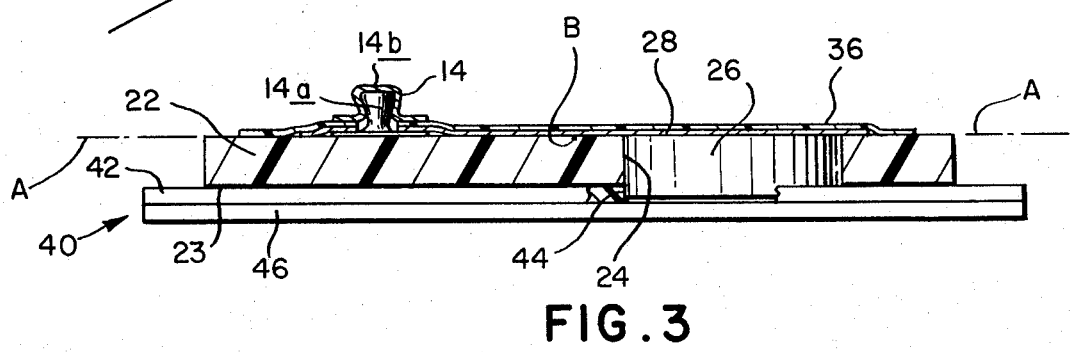
FIG. 3

MEDICAL ELECTRODE

BACKGROUND OF THE INVENTION

This application relates to medical electrodes. It relates more specifically to disposable medical electrodes which are temporarily secured to a patient's body to provide conductive contact between the patient's skin and medical monitoring equipment.

Conventionally, these electrodes employ a thin base layer of compliant material which supports an electrical contact usually in the form of a male metallic snap fastener element. The base layer also supports a pad filled with conductive gel in intimate contact with the base of the snap fastener element.

The underside of the base layer is coated with a suitable adhesive and when the base layer is adhered to the patient's skin, the gel pad is pressed against the skin with the conductive gel making good electrical contact between the skin and the snap fastener element. Electrical connection between the monitoring apparatus is then made by attaching the snap fastener element to a mating fastener element connected to the apparatus. A typical prior disposable electrode is shown, for example, in U.S. Pat. No. 3,828,766, dated Aug. 13, 1974.

While these disposable electrodes are a vast improvement over the suction cup-type electrodes used previously, they still have some drawbacks. More particularly, in many instances, as when a patient is moved from one place to another, it is necessary to make repeated connections to monitoring apparatus after the electrode has been adhered to the patient's skin. This invariably results in movement of the snap fastener element and the underlying gel pad which, in turn, disturbs and even interrupts the conductive path between the element and the patient's skin.

In other instances, such as in stress testing, the patient must move relative to the equipment while his body signs are being monitored. Consequently, the electrical lead connected to the electrode causes movement of the snap fastener element relative to the gel pad, giving rise to electrical noise which degrades the output signals from the patient's body.

Another problem with prior pregelled medical electrodes stems from the fact that many electrolyte gels contain salt that tends to corrode the snap fastener element. To avoid the drop in conductivity and electrical noise incident to such corrosion, some electrodes are provided with silver or silverplated fastener elements which increase the overall cost of the product. Another type of electrode which we are aware of incidentally avoids this problem by placing the fastener element at one end of a long insulated wire whose other end makes connection with the electrode gel pad inside a large rigid housing at the center of the electrode. However, this solution to the corrosion problem generates further difficulties. More particularly, the long wires from the different electrodes tend to become tangled so that it is hard to locate them and to properly connect the fastener element to the correct channel of the monitoring apparatus. Further, the long leads may inadvertently be pulled when disconnected from the monitoring apparatus as when the patient is moved, thereby upsetting the conductive contact between the electrode and the skin. Also, the presence of the rigid connector housing on the electrode increases the overall size and weight of the electrode and increases patient discomfort.

SUMMARY OF THE INVENTION

Accordingly, the present invention aims to provide a disposable medical electrode to which repeated connections can be made without disturbing its conductive contact with the patient's skin.

Another object of the invention is to provide a disposable medical electrode which minimizes noise artifacts due to movement of the patient relative to the monitoring equipment to which he is connected.

A further object of the invention is to provide a medical electrode of this general type having good impedance and d.c. offset characteristics.

Still another object of the invention is to provide a pregelled medical electrode having a standard low cost metallic contact element which is not subject to gel corrosion.

Yet another object of the invention is to provide a disposable medical electrode whose gel remains moist for a long time and which is convenient to apply and comfortable to wear.

Other objects will in part be obvious and will in part appear hereinafter.

The invention accordingly comprises the features of construction, combination of elements and arrangement of parts which are exemplified in the construction hereinafter set forth, and the scope of the invention will be indicated in the claims.

In general, the disposable electrode of this invention includes a thin support layer of compliant material, one surface of which is adhesive. The support layer supports a conductive gel pad at a first location in the plane of the support layer with a portion of the gel pad being exposed at the adhesive surface of the support layer. The support layer also supports an electrical contact element at a second location in the plane of the support layer which is offset from the first location and so that the contact element is exposed at another surface of the support layer. Finally, the support layer supports a flexible conductor extending between the two locations on the support layer. The conductor is in intimate electrical contact with the gel pad and is also electrically connected to the contact element so that there is a conductive path between the contact element and gel pad without the two being in physical contact.

In a preferred embodiment of the invention, the support layer is a thin, closed-cell, foam plastic wafer having a relatively large opening extending between its top and bottom surfaces. The electrode gel pad, in the form of a small, open-cell, plastic foam wafer, is snugly received in this opening.

A metallic snap fastener element is connected to one end of a strip of silver foil and the two are positioned on the top surface of the support layer so that the opposite end of the silver strip contacts the exposed end of the gel pad. Thus, the fastener element and gel pad are spaced-apart or offset from one another on the support layer. A thin, nonporous, vinyl plastic sheet having an access opening for the fastener element is adhered to the top of the support layer so that it secures the fastener element and foil strip to the support layer and also reinforces the support layer.

After the gel pad is impregnated with conductive electrolyte gel, a releasable cover is adhered to the underside of the support member to maintain the gel pad in a wet conductive condition.

When using the electrode, its cover is stripped away and the support layer adhered to the proper location on the patient's body with the gel pad being pressed into intimate contact with the patient's skin. Then, the mating snap fastener element leading to the monitoring equipment is attached to the snap fastener element on the electrode. Since that attachment occurs away from the gel pad, any movement of the fastener elements incident to attachment does not upset the conductive path between the fastener element and the patient's skin. Thus, repeated connections can be made to the electrode without adversely affecting the electrical signals applied to the monitoring equipment. Also, the patient can move about without excessive electrical noise being produced.

Further, since the fastener element is offset from the gel pad, an inexpensive steel fastener element can be used without any danger of gel corrosion and resultant signal degradation. Of course, there is no corrosion problem with the conductive strip which does contact the gel pad because it is made of silver foil which is not corroded by the gel. Rather, the foil forms with a salt-containing gel a silver-silver chloride contact boundary which actually enhances electrode conductivity.

Since the gel pad is recessed into the closed cell foam support layer and its top is covered by the nonporous vinyl sheet, only a relatively small part of its total area is exposed. Accordingly, the gel pad will remain in a wet conductive condition for a relatively long time after the electrode's protective cover is removed. For this same reason, the overall electrode has a very low profile and is very conforming so that it can be worn comfortably for a relatively long period of time.

BRIEF DESCRIPTION OF THE DRAWING

For a fuller understanding of the nature and objects of the invention, reference should be had to the following detailed description taken in connection with the accompanying drawing, in which:

FIG. 1 is a perspective view of a disposable medical electrode made in accordance with this invention;

FIG. 2 is an exploded perspective view on a much larger scale showing the elements of the electrode in greater detail; and FIG. 3 is a view of the FIG. 1 electrode in medial section with parts shown in elevation.

DESCRIPTION OF THE PREFERRED EMBODIMENT

Referring to FIG. 1 of the drawing, the disposable electrode of this invention, shown generally at 10, is adhered to the surface of a patient's body shown in dotted lines at 12. The electrode 10 conforms to the contour of the body as shown to provide a good conductive path between a skin area underlying the electrode and an electrical contact in the form of a conductive male snap fastener element 14 projecting from the top of the electrode.

Monitoring apparatus (not shown) is coupled to the electrode by means of an electrical lead 16 which terminates in a mating conductive snap fastener element 18 coupled to element 14.

As will be seen presently, the snap fastener element 14 is situated on the electrode an appreciable distance from the skin area conductively contacted by the electrode's gel pad so that any movements of element 14 incident to coupling or uncoupling element 18 or to movement of the lead 16 do not tend to upset the conductive contact between the electrode 10 and the patient's skin. Also, movements of the electrode 10 relative to its electrical lead 16 when the patient moves produces fewer spurious noise signals that might tend to mask the useful body signals being monitored. Such noise is further minimized because the contact element cannot be corroded by the electrolyte in the relatively remote gel pad.

As seen from FIG. 1, electrode 10 is quite compliant so that it readily conforms to the curvature of the patient's body. Further, the only rigid element in the entire electrode 10 is the snap fastener element which is quite small and positioned at the top of the foam plastic base layer away from the patient's skin. Consequently, there are no hard, unyielding surfaces near the patient's skin.

Also, the entire underside of the electrode 10 presented to the patient's body constitutes essentially a single flat surface. This adds to patient comfort, and also permits one to use a simple flat strip as a cover as opposed to the preformed cup-shaped cover members required by prior electrodes such as the one disclosed in the aforesaid patent. For the same reason, the electrode has a very low profile as compared with prior comparable electrodes of this general type so that it does not tend to be pulled away inadvertently because it catches on some obstruction as the patient moves.

Turning now to FIGS. 2 and 3, electrode 10 comprises a relatively soft, compliant support layer 22 in the form of a thin wafer of closed cell plastic foam material such as closed cell polyurethane or polyethylene plastic. In the illustrated embodiment, layer 22 is ovular, having a approximately 2 ¼ inch major axis A and a 1 ⅝ inch minor axis B, and is about ⅛ inch thick.

The underside of layer 22 is provided with a conventional medical adhesive coating 23.

A generally circular through opening 24 is formed in support layer 22. Opening 24 is displaced from the center of layer 22 along its major axis A. Typically, the opening has a diameter on the order of ¾ inch with its center being about 5/16 inch from the center of layer 22.

Opening 24 snugly receives a soft, compliant gel pad 26 in the form of a small wafer of open cell plastic foam material such as open cell polyurethane plastic. Pad 26 is designed to be permeated with the usual conductive electrolyte gel such as Redux cream or any other conveniently available gel.

If desired, gel pad 26 can be slightly larger in diameter than opening 24 so that when it is inserted into the opening as shown in FIG. 3, it is retained there by the compressive engagement provided by the wall of opening 24. Also, the pad can be made slightly thicker than the support layer 22 so that, in its uncompressed state, it projects somewhat beyond the underside of base layer 22 as best seen in FIG. 3.

The snap fastener element 14 is of a conventional design and is actually composed of two parts; to wit, an eyelet 14a and a mating stud 14b which are arranged to be press-fit together as seen in FIG. 3. In the present electrode, eyelet 14a is positioned on base layer 22 along its major axis A, but at the opposite end thereof from gel pad 26. Consequently, it is spaced appreciable from the gel pad as best seen in FIG. 3. Typically, the center of the fastener element is on the order of 13/16 inch from the center of opening 24.

A thin silver foil strip 28 provides the conductive path between the gel pad and the snap fastener element. In one embodiment, the strip is 1 ¼ inches long and 3/16 inch wide.

During assembly of electrode 10, eyelet 14a is inserted through a small opening 32 near one end of foil strip 28 and the strip is positioned on base layer 22 so that its longitudinal axis coincides with axis A and so that its opposite end extends slightly beyond the far edge of opening 24. Also, the strip 28 is almost as wide as opening 24 so that it contacts the gel pad therein over a large percentage of its top surface area to insure intimate electrical contact with the gel pad.

After the strip 28 is in place, a paper-thin sheet 36 of a strong, flexible plastic such as vinyl plastic is adhered to the top surface of base layer 22. Preferably, sheet 36 is the same shape as layer 22 and has the same or slightly smaller dimensions as illustrated so that it completely covers the foil strip 28. Since the foil strip is somewhat narrower than opening 24, the adhesive sheet 36 adheres to portions of pad 26 on each side of the strip and so helps to retain the pad in opening 24.

A small opening 38 is provided in the sheet 36 to accommodate the tip of eyelet 14a projecting through foil strip 28. Then the stud 14b is pressed down onto the exposed tip of eyelet 14a to complete the electrode. When the stud and eyelet are fastened together in this manner, the portion of the conductive strip 28 around its opening 32 is pressed tightly against the conductive surface of eyelet 14a so that good electrical contact is assured between the strip and element 14.

Alternatively, electrical contact between element 14 and the foil strip may be made by placing the strip under eyelet 14a instead of on top of the eyelet as shown. In this case, of course, opening 32 can be eliminated.

As best seen in FIG. 3, the adhesion of the sheet 36 to the top surface of support layer 22 reinforces that layer while preserving its compliance and flexibility. It also maintains strip 28 in intimate physical and thus electrical contact with the gel pad seated in opening 24. Finally, sheet 36 being nonporous seals the upper end of opening 24. This, coupled with the fact that the support layer 22 is made of a nonporous closed cell material, minimizes drying out of the electrolyte gel at either the sides or the top of the gel pad 26. Consequently, the pad remains in a conductive wet condition for a relatively long time, even though its underside may be exposed.

Usually, the underside of disposable electrodes of this general type are covered by releasable nonporous covers prior to use. This cover protects the adhesive coating 23. It also seals the exposed underside of the gel pad 26 so that the electrode can be pregelled and stored for a long period without the gel pad drying out and thus losing its conductive properties.

In the illustrated embodiment, the cover is shown generally at 40 and comprises a liner mat 42 which is slightly larger than electrode 10 and made of a material which releases from adhesive coating 23. An opening 44 is provided in the liner mat directly below opening 24 to accommodate the portion of the gel pad 26 projecting slightly below the underside of the base layer 22. A nonporous paper-thin plastic cover strip 46 of the same size and shape as the liner mat 42 is then adhered to the underside of the mat completely covering gel pad 26. Since the liner mat and cover strip are made from flat sheet stock and are not formed pieces, they do not add appreciably to the cost of the product or to its thickness.

It will be seen from the foregoing, then, that my improved disposable electrode whose contact element is offset from the gel pad provides definite advantages over prior comparable electrodes of this general type. It has the same or better impedance and d.c. offset characteristics yielding good conductivity and base line stability. It presents no problem of contact element corrosion. It suffers no appreciable change in conductivity when the contact element is repeatedly connected to and disconnected from the monitoring equipment and no noise artifacts are produced when the contact element 14 is moved as the patient moves. Finally, the entire electrode is extremely compact and compliant so that is readily conforms to the curvature of the patient's body and can be worn comfortably for a long period of time.

It will thus be seen that the objects set forth above, among those made apparent from the preceding description, are efficiently attained and, since certain changes may be made in the above electrode without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described.

I claim:
1. A medical monitoring electrode comprising
   A. a flexible support layer having a first surface and a second surface,
   B. an adhesive applied to the first surface,
   C. a contact element supported by the support layer and exposed at the second surface, said contact element comprising
      1. a conductive snap fastener stud, and
      2. a conductive snap fastener eyelet press-fit into the stud,
   D. a flexible conductive gel pad
      1. supported by the support layer at a location thereon spaced across the layer an appreciable distance from the contact element, so that said gel pad is not in physical contact with the contact element, and
      2. having respective end portions exposed at the first and second surfaces of the support layer,
   E. an electrical conductor
      1. supported by the second surface of the support layer, and
      2. extending between the contact element and the gel pad forming a conductive path between the two, and
   F. a thin flexible nonporous cover sheet
      1. adhered to the second surface of the support layer,
      2. covering the conductor and the end portion of the gel pad exposed at said second surface, and
      3. having an access opening through which said contact element protrudes so that electrical connection can be made thereto.
2. The electrode defined in claim 1 wherein
   A. the support layer has an opening extending between said two surfaces,
   B. the gel pad is snugly received in said opening, and
   C. the electrical conductor is a relatively wide flexible foil strip having
      1. one end portion contacting a relatively large area of the gel pad exposed at the second surface of the support layer, and

2. its other end connected electrically to the contact element.

3. The electrode defined in claim 2 and further including a conductive electrolyte gel permeating the gel pad.

4. The electrode defined in claim 3 wherein
   A. the support layer is made of a closed cell plastic foam material, and
   B. the gel pad is made of an open cell plastic foam material.

5. The electrode defined in claim 4 and further including a releasable cover
   A. adhered to the first surface of the support layer, and
   B. covering the portion of the gel pad exposed at said first surface.

6. The electrode defined in claim 2 wherein the foil strip is narrower than the width of the opening in the support layer and the gel pad is exposed on each side of the strip so that the cover sheet adheres to portions of the gel pad exposed on each side of the strip at the second surface of the support layer.

7. The electrode defined in claim 2 wherein the foil strip and cover sheet are sandwiched between the stud and eyelet of said contact element.

8. The electrode defined in claim 2 wherein the foil strip is made of silver metal.

9. The electrode defined in claim 2 wherein the gel pad is slightly thicker than the support layer so that it projects somewhat from the opening at the first surface of the support layer.

10. The electrode defined in claim 9 wherein the gel pad is slightly larger in area than the opening in the support layer so that it is retained in the opening in the support layer by the compressive engagement with the opening wall.

11. The electrode defined in claim 1 wherein
    A. the support layer is elongated, and
    B. the contact element and gel pad are spaced apart along the major axis of the support layer.

\* \* \* \* \*